(12) United States Patent
Mahon et al.

(10) Patent No.: US 7,296,567 B2
(45) Date of Patent: Nov. 20, 2007

(54) BREATH ACTUATED AEROSOL DISPENSERS

(75) Inventors: Gary D. Mahon, Wilford (GB); Eric A. Baum, Loughborough (GB); Andrew M. Bryant, Kneesworth (GB)

(73) Assignee: 3M Innovative Properties Company, St. Paul, MN (US)

( * ) Notice: Subject to any disclaimer, the term of this patent is extended or adjusted under 35 U.S.C. 154(b) by 315 days.

(21) Appl. No.: 10/529,324

(22) PCT Filed: Sep. 15, 2003

(86) PCT No.: PCT/US03/29356

§ 371 (c)(1),
(2), (4) Date: Mar. 25, 2005

(87) PCT Pub. No.: WO2004/028608

PCT Pub. Date: Apr. 8, 2004

(65) Prior Publication Data

US 2006/0037611 A1    Feb. 23, 2006

(30) Foreign Application Priority Data

Sep. 25, 2002   (GB) .................................. 0222295.8

(51) Int. Cl.
*A61M 11/00* (2006.01)
(52) U.S. Cl. ............................. 128/200.14; 128/200.23
(58) Field of Classification Search ........... 128/200.14, 128/200.23, 204.23, 204.26, 202.22
See application file for complete search history.

(56) References Cited

U.S. PATENT DOCUMENTS

| 3,157,179 | A | | 11/1964 | Paullus et al. |
| 4,803,978 | A | | 2/1989 | Johnson, IV et al. |
| 4,819,834 | A | | 4/1989 | Thiel |
| 5,119,806 | A | * | 6/1992 | Palson et al. ........... 128/200.14 |
| 5,217,004 | A | * | 6/1993 | Blasnik et al. ......... 128/200.23 |
| 5,447,150 | A | | 9/1995 | Bacon |
| 5,826,571 | A | | 10/1998 | Casper et al. |
| 6,553,988 | B1 | * | 4/2003 | Holroyd ................. 128/200.23 |

FOREIGN PATENT DOCUMENTS

| EP | 0 147 028 | 7/1985 |
| EP | 0 186 280 | 7/1986 |
| GB | 1 269 554 | 4/1972 |
| GB | 1 288 971 | 9/1972 |
| GB | 1 297 993 | 11/1972 |
| GB | 1 335 378 | 10/1973 |
| GB | 1 383 761 | 2/1975 |
| GB | 1 392 192 | 4/1975 |
| GB | 1 413 285 | 11/1975 |
| GB | 2 204 799 | 11/1988 |
| WO | 85/01880 | 5/1985 |
| WO | 96/28376 | 9/1996 |
| WO | 01/93933 | 12/2001 |

OTHER PUBLICATIONS

"L'Aerosol-Dosuer Prolair Autohaler" Annales Francaises De Chronometrie et de Microtechnique, Observatoire de Besancon, Besancon, Fr., vol. 47, 1998, pp. 115-121, XP 000830922.

* cited by examiner

*Primary Examiner*—Steven O. Douglas

(57) ABSTRACT

A breath actuated metered dose inhaler device for use with an aerosol valve having a transient metering chamber.

6 Claims, 3 Drawing Sheets

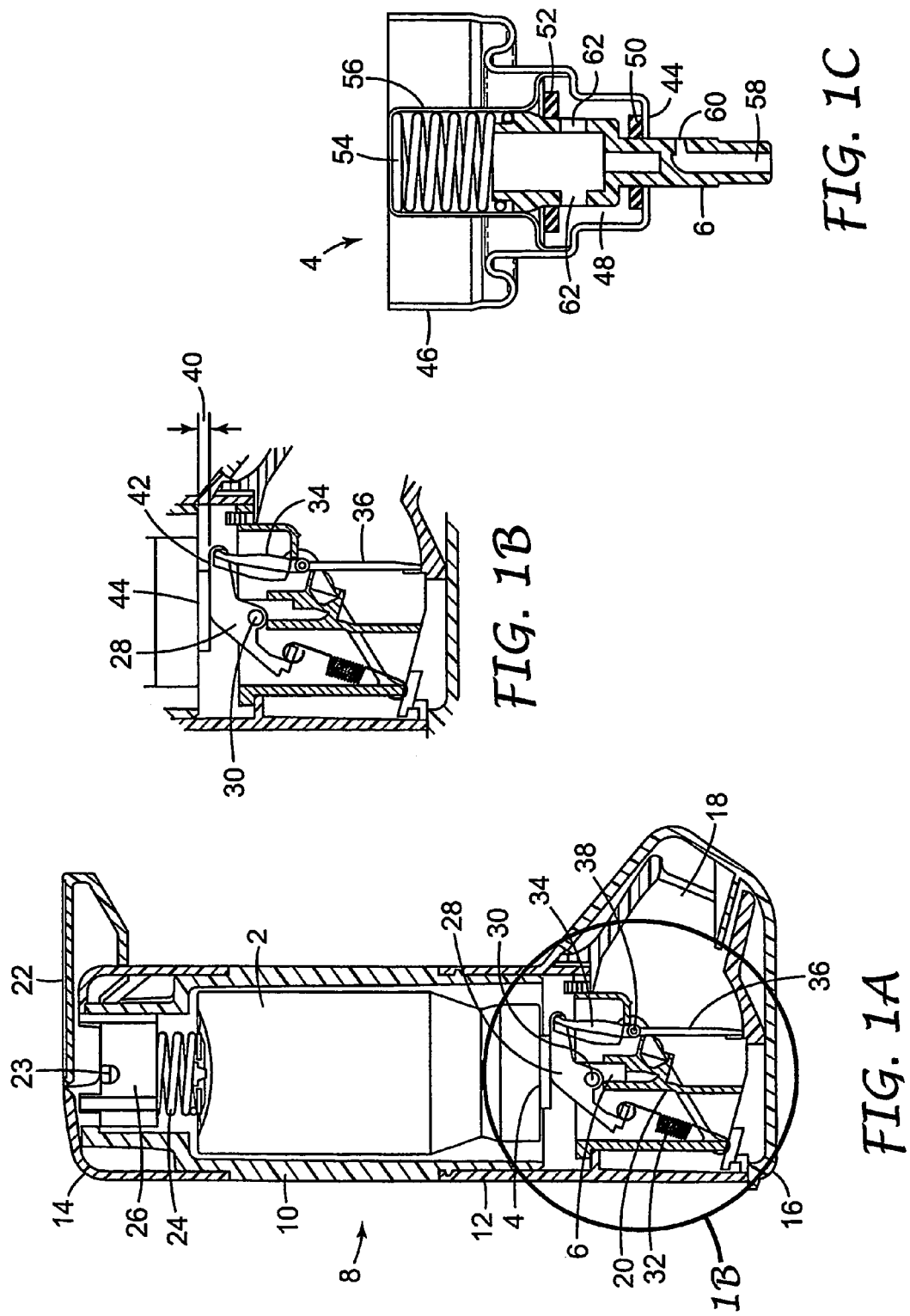

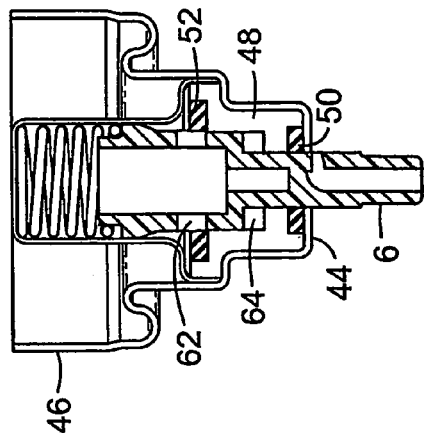
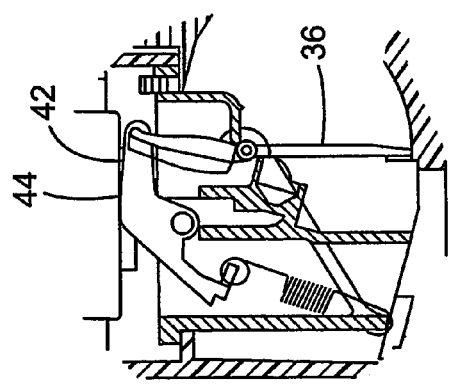
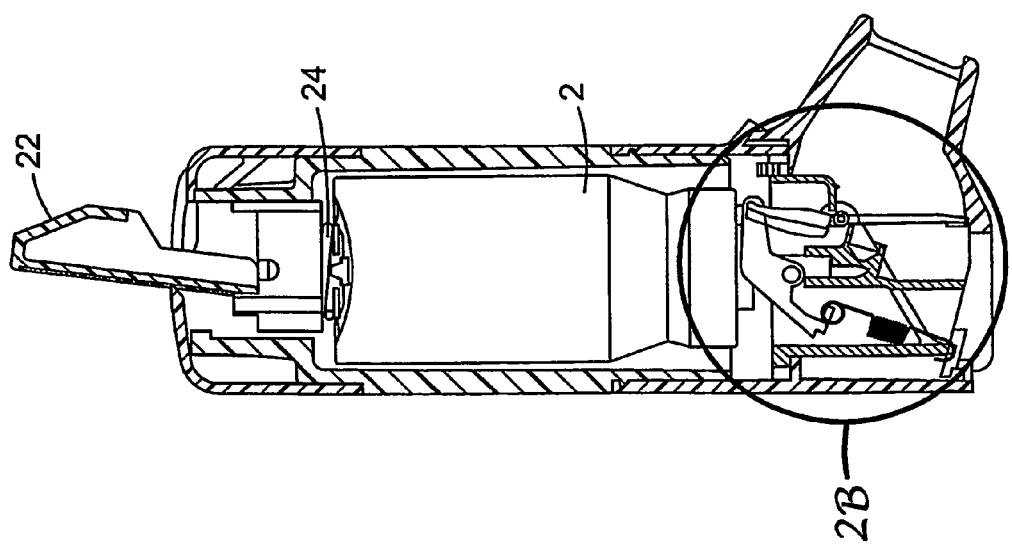

BREATH ACTUATED AEROSOL DISPENSERS

This invention relates to breath actuated medicament dispensing devices of the type where a metered dose of medicament is administered to the respiratory system of a patient in response to the inhalation of the patient.

Metering valves are a common means by which aerosols are dispensed from aerosol containers. Metering valves are particularly useful for administering medicinal formulations that include a liquefied gas propellant and are delivered to a patient in an aerosol.

In some metering valves, the metering chamber fills with the medicinal formulation prior to the patient actuating the valve stem and thereby releasing the dose. The metering chamber is refilled with formulation after dispensing one dose so that the metering valve is ready to discharge the next dose. Consequently, the metering chamber contains formulation at all times except for the brief time during which the valve stem is depressed by the user to discharge a dose.

In other metering valves the metering valve is designed such that the metering chamber does not materialise unless and until the valve stem is actuated. Examples of such valves are disclosed in U.S. Pat. No. 4,819,834. Actuation of these valve stems can be divided into a filling stage and a discharge stage. The filling stage begins as the valve stem is depressed during actuation. The action of depressing the valve stem causes the formation of a transient metering chamber, which is in fluid communication with the residual metering volume defined by the small annular gap. As the valve stem is depressed, the transient portion of the metering chamber expands and formulation enters the metering chamber. As displacement of the valve stem continues, a stage is reached at which filling of the transient metering chamber stops.

Eventually, displacement of the valve stem continues to the discharge stage, in which the metered formulation is discharged. In these valves, a single actuation thus causes rapid filling of the transient metering chamber followed by discharge of the formulation to the patient. Generally, metered formulation does not reside for any appreciable amount of time in the metering chamber in these metering valves.

While a metering valve having a transient metering chamber provides advantages over other types of metering valves for the delivery of aerosol formulations, it has now been appreciated that the flow of formulation from the container to the metering chamber may be disrupted or impeded. Flow through regions of significantly restricted access, such as narrow annular passageways and/or entrance ways to the metering chamber, may be impeded sufficiently to give rise to substantially incomplete filling of the metering chamber. If this happens, formulation may be delivered in inconsistent or inaccurate doses. In particular, it has now been appreciated that the time available for filling the metering chamber also has a significant effect on the ability to completely fill the transient metering chamber. The time available for filling depends on the speed at which the valve stem is depressed. In the so-called "press-and-breathe" devices in which the patient manually depresses the aerosol container relative to the valve stem to fire the valve the speed at which the valve stem is depressed is generally not more than 100 mm/sec. However, breath actuated inhalers typically fire the valve more rapidly than manual firing e.g. with valve stem speeds in the range 165 to 330 mm/sec. Thus, there are difficulties associated with the use of metering valves having a transient metering chamber with breath actuated devices.

A common feature of many known breath actuation devices is that they involve two stages of operation: a priming stage in which a priming force is applied to the valve stem but actuation of the valve stem is prevented; and a firing stage in which the priming force is released resulting in movement of the valve stem to fire the valve. The priming stage is generally a manual operation and may involve some movement of the valve stem but not sufficient to fire the valve. Any movement of the valve stem in the priming stage tends to be at relatively low speed. Once the device is triggered by inhalation there is high speed displacement of the valve stem under the priming force.

SUMMARY

It has now been found that if the metering and firing stages of operation of a metering valve of the type having a transient metering chamber are synchronised with the priming and firing stages of a breath actuated device, any difficulties or problems associated with flow of formulation to fill the metering chamber may be overcome or at least significantly reduced.

Therefore according to the present invention there is provided a breath actuated medicament dispensing device comprising:

- an aerosol container containing a pressurised medicament formulation equipped with a metered dose dispensing valve having a movable valve stem;
- a housing disposed about the aerosol container;
- a patient port in communication with the dispensing valve;
- priming means adapted to apply a bias to the valve stem relative to the aerosol container sufficient to move the valve stem to fire the valve; restraining means movable between a blocking position in which it prevents said bias firing the valve and a release position in which it allows said bias to fire the valve;
- trigger means responsive to inhalation through the patient port to cause the restraining means to move from its blocking position to its release position; wherein the aerosol valve comprises:
- a valve housing;
- a tank component positioned within the valve housing; and
- a valve stem mounted within said valve housing and tank component sequentially movable between a first position, a second position and a third position as the valve stem is depressed in a single direction;

such that:

- as the valve stem is moved from said first position towards, said second position a metering chamber is formed and defined between the valve stem and tank component and formulation flows from the aerosol container into the metering chamber;
- in said second position the metering chamber has a predetermined volume and is sealed from the aerosol container; and
- in said third position formulation is released from the metering chamber through the valve stem; and wherein:
- the priming means is constructed and arranged such that as the device is primed by operating said priming means the valve stem is moved from its first to its second position to allow formation and filling of the metering chamber;
- the restraining means is constructed and arranged such that in its blocking position it maintains the valve stem in its second position until the trigger means is actuated by inhalation through the patient port.

The invention provides a simple effective means of overcoming problems associated with filling the metering chamber of an aerosol valve of the type having a transient metering chamber by controlling the movement of the valve stem from its first to second position by the priming and restraining means of a breath actuated device. When the breath actuated device has been primed the valve stem is held in its second position with the metering chamber completely full of formulation ready to be dispensed. The priming stage of the breath actuated device is sufficiently slow to allow the metering chamber to be filled as it is created by movement of the valve stem.

The invention is applicable to a wide range of breath actuated devices including those in which the restraining means comprises a latch mechanism and those in which the restraining means comprises means for applying a resisting pneumatic force.

In general, the aerosol container will be mounted in the dispensing device with the valve stem located in a fixed nozzle block. A priming force is applied to the base of the aerosol container e.g. by compression of a spring. When the device is primed by compressing the spring e.g. by moving a lever to an over centre position, there is movement of the aerosol container relative to the valve stem causing the valve stem to be partially depressed before the restraining means is engaged to prevent further movement. The device is arranged such that this initial movement of the valve stem relative to the aerosol container is sufficient to form and completely fill the metering chamber in the valve. The valve is held in its second position until the device is actuated by the patient inspiring through the patient port. Patient inspiration actuates the trigger which allows movement of the restraining means to its release position and thereby allows relative movement of the valve stem and aerosol container under the influence of the bias causing the valve to fire.

In another embodiment of the invention the aerosol container is fixed within the housing and the priming force is applied to the valve stem e.g. to a movable nozzle block which is mounted on the valve stem.

BRIEF DESCRIPTION OF THE DRAWINGS

The invention will now be described with reference to the accompanying drawings in which:

FIG. 1A represents a vertical cross-section through an embodiment of a dispensing device in accordance with the invention in its first position, FIG. 1B shows the restraining and triggering means of the device and FIG. 1C is a cross-section through the aerosol valve in its first position;

FIGS. 2A, 2B and 2C represent similar views to FIG. 1 with the device in its primed position and the aerosol valve in its second position.

DETAILED DESCRIPTION

Figure 3B:
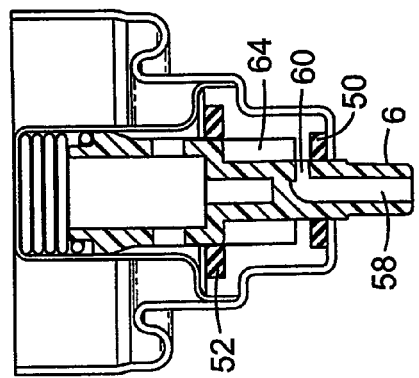
FIG. 3A shows the device of FIG. 1 in its fired position and FIG. 3B shows the aerosol valve in its third (fired) position.

The invention will be described with reference to a breath actuated device which is described in EP 0147028. However, it will be appreciated that the invention may use other variants of breath actuated devices, such as those described in GB 1288971, GB 1297993, GB 1335378, GB 1383761, GB 1392192, GB 1413285, WO85/01880, GB 2204799, U.S. Pat. No. 4,803,978, EP 0186280, GB 1269554, U.S. Pat. No. 5,447,150 and WO 01/93933.

In the drawings, like references represent like parts.

FIG. 1A shows a cross section through a breath actuated device in its rest position. The device comprises an aerosol container (2) containing a pressurised medicament formulation and equipped with a metered dose dispensing valve (4) having a movable valve stem (6). A housing (8) is disposed about the aerosol container (2) and comprises a sleeve (10), body (12), top (14) and a mouthpiece cover (16) which covers the patient port (18). The valve stem (6) is positioned within a nozzle block (20) which directs formulation from the valve stem towards the patient port (18).

The priming means comprises a priming lever (22) which is pivotally mounted about axis (23) to act upon priming spring (24) secured within a cage (26). In the rest position shown in FIG. 1A, the priming spring (24) exerts little or no bias on the aerosol container (2).

The restraining means comprises a rocker (28) pivotally mounted about axis (30). One end of the rocker is attached to tension spring (32) and the other is pivotally connected to catch (34). The other end of catch (34) rests on a cam surface of vane (36) which acts as the trigger mechanism. Vane (36) is pivotally mounted at axis (38).

In the rest position shown in FIG. 1B there is a clearance (40) between the upper surface (42) of the rocker (28) and the lower surface (44) of the valve ferrule.

FIG. 1C is on an enlarged scale compared with FIG. 1A and shows a cross-section through the aerosol valve in its first position when the device is in its rest position as shown in FIG. 1A.

The valve (4) comprises a valve housing (46), a tank component (48) positioned within the valve housing and a valve stem (6) mounted within the valve housing and tank component. The valve comprises outer seal (50) and inner seal (52). The valve stem (6) is biased towards its first position shown in FIG. 1C by compression spring (54) held within spring retaining sleeve (56).

The outer portion of the valve stem (6) comprises a discharge passage (58) and side pierce (60). The inner portion of the valve stem is shaped to completely fill the tank component (48) when the valve stem is in its first position. The inner portion of the valve stem is hollow, in communication with the aerosol container and comprises sampling ports (62). When the valve stem is in its first position shown in FIG. 1C there is no metering chamber formed.

FIGS. 2A and 2B show the device in its primed position. Priming lever (22) is pivoted upwardly causing spring (24) to be compressed applying a bias to the aerosol container (2). The aerosol container moves downwardly under the influence of the bias until the lower surface (44) of the valve ferrule contacts the upper surface (42) of the rocker (28). The rocker (28) is unable to pivot since it is blocked by the catch (34) that engages the vane (36). During the priming operation the aerosol container moves by the distance of the clearance (40) shown in FIG. 1B.

During the priming operation the valve moves from its first position shown in FIG. 1C to its second position shown in FIG. 2C. During movement of the valve stem from its first to its second position a metering chamber (64) is formed between the inner portion of the valve stem (6) and the tank component (48). The metering chamber is filled with formulation from the aerosol container passing through the sampling port (62) and through a small annular gap (not shown) between the inner portion of the valve stem (6) and the tank component (48) into the metering chamber (64). Formulation is prevented from exiting the metering chamber (64) by the outer seal (50) that is in sealing engagement with the valve stem and between the tank component (48) and the valve housing (46). In the second position of the valve stem shown in FIG. 2, inner seal (52) is in sealing engagement with the valve stem thereby preventing formulation passing through the sampling port (62). In the second position of the valve stem shown in FIG. 2C the metering chamber has been fully formed and completely filled with the formulation.

Figure 3A:
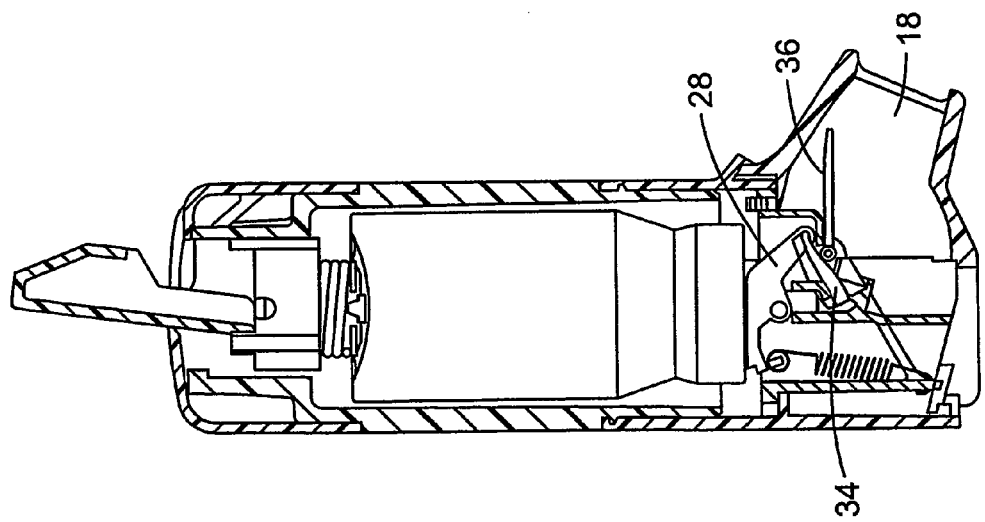

FIG. 3A shows the device in its fired position. Inhalation through the patient port (18) causes vane (36) to pivot upwardly. Movement of the vane (36) displaces the end of catch (34) from the vane thereby moving the constraint on rocker (28). Rocker (28) pivots due to the force exerted on it by the valve ferrule under the influence of the priming spring (24) thereby allowing the aerosol container (2) to move downwardly, causing the valve to fire.

FIG. 3B shows the valve in its firing position. The valve stem (6) has moved inwardly such that the side pierce (60) passes through the outer seal (50) thereby allowing the contents of the metering chamber to pass through the side pierce (60) and discharge passage (58). The inner seal (52) remains in sealing engagement with the inner portion of the valve stem preventing communication between the metering chamber (64) and the aerosol container.

It will be appreciated that the speed of movement during the firing, i.e. movement of the valve stem from its second to its third position, will not affect the performance of the valve since the metering chamber was formed and completely filled during the priming stage. Thus high speed movement under the influence of the priming spring during the firing operation has no effect on the volume of formulation dispensed.

It will be understood that the present disclosure of particular embodiments in accordance with the invention is for the purpose of illustration only and the invention extends to modifications, variations and improvements thereof.

The invention claimed is:

1. A breath actuated medicament dispensing device comprising:
    an aerosol container containing a pressurised medicament formulation equipped with a metered dose dispensing valve having a movable valve stem;
    a housing disposed about the aerosol container;
    a patient port in communication with the dispensing valve;
    a priming mechanism adapted to apply a bias to the valve stem relative to the aerosol container sufficient to move the valve stem to fire the valve;
    a restraining mechanism movable between a blocking position in which it prevents said bias firing the valve and a release position in which it allows said bias to fire the valve; and
    a trigger assembly responsive to inhalation through the patient port to cause the restraining mechanism to move from its blocking position to its release position;
wherein the aerosol valve comprises:
    a valve housing;
    a tank component positioned within the valve housing; and
    a valve stem mounted within said valve housing and tank component sequentially movable between a first position, a second position and a third position as the valve stem is depressed in a single direction;
such that:
    as the valve stem is moved from said first position towards said second position a metering chamber is formed and defined between the valve stem and tank component and formulation flows from the aerosol container into the metering chamber;
    in said second position the metering chamber has a predetermined volume and is sealed from the aerosol container; and
    in said third position formulation is released from the metering chamber through the valve stem;
and wherein:
    the priming assembly is constructed and arranged such that as the device is primed by operating said priming assembly the valve stem is moved from its first to its second position to allow formation and filling of the metering chamber;
    the restraining mechanism is constructed and arranged such that in its blocking position it maintains the valve stem in its second position until the trigger assembly is actuated by inhalation through the patient port.

2. A breath actuated medicament dispensing device as claimed in claim 1 in which the priming assembly comprises a spring.

3. A breath actuated medicament dispensing device as claimed in claim 1 in which the valve stem is located within a nozzle block and the priming assembly applies a bias to the aerosol container.

4. A breath actuated medicament dispensing device as claimed in claim 1 in which the restraining mechanism comprises a latch and the triggering assembly comprises a vane.

5. A breath actuated medicament dispensing device as claimed in claim 4 in which the vane is positioned within the patient port.

6. A breath actuated medicament dispensing device as claimed in claim 1 in which the restraining mechanism applies a resisting pneumatic force to prevent firing of the valve under the influence of the priming assembly.

* * * * *

UNITED STATES PATENT AND TRADEMARK OFFICE
CERTIFICATE OF CORRECTION

PATENT NO. : 7,296,567 B2  Page 1 of 1
APPLICATION NO. : 10/529324
DATED : November 20, 2007
INVENTOR(S) : Gary D. Mahon It is certified that error appears in the above-identified patent and that said Letters Patent is hereby corrected as shown below:

Col. 1, Line 3: Below "DISPENSERS" insert -- BACKGROUND --.

Signed and Sealed this

Twenty Second Day of April, 2008

JON W. DUDAS
*Director of the United States Patent and Trademark Office*